(12) United States Patent
Greszczuk

(10) Patent No.: US 7,051,597 B2
(45) Date of Patent: May 30, 2006

(54) APPARATUS AND METHODS FOR TENSION TESTING OF CURVED SPECIMENS

(75) Inventor: Longin B. Greszczuk, Mission Viejo, CA (US)

(73) Assignee: The Boeing Company, Chicago, IL (US)

( * ) Notice: Subject to any disclaimer, the term of this patent is extended or adjusted under 35 U.S.C. 154(b) by 0 days.

(21) Appl. No.: 10/719,147

(22) Filed: Nov. 21, 2003

(65) Prior Publication Data
US 2005/0109124 A1 May 26, 2005

(51) Int. Cl.
*G01N 3/08* (2006.01)

(52) U.S. Cl. .................................................... 73/831

(58) Field of Classification Search .............. 73/831, 73/832, 856
See application file for complete search history.

(56) References Cited

U.S. PATENT DOCUMENTS

| | | | |
|---|---|---|---|
| 4,552,024 A | 11/1985 | Baker et al. | |
| 4,566,335 A * | 1/1986 | Singhal | 73/849 |
| 4,748,854 A * | 6/1988 | Rao | 73/799 |
| 4,926,692 A | 5/1990 | Brokowski et al. | |
| 5,007,291 A | 4/1991 | Walters et al. | |
| 5,170,366 A | 12/1992 | Passarelli | |
| 5,305,634 A * | 4/1994 | Suga et al. | 73/86 |
| 6,523,418 B1 * | 2/2003 | Bray | 73/801 |
| 6,810,751 B1 * | 11/2004 | Moreno et al. | 73/849 |

* cited by examiner

*Primary Examiner*—Max Noori
(74) *Attorney, Agent, or Firm*—Lee & Hayes, PLLC

(57) ABSTRACT

Apparatus and methods for tension testing of curved composite specimens are disclosed. In one embodiment, an apparatus for tension-testing first and second curved specimens includes a first end member adapted to be coupled to first end portions of the first and second curved specimens, and a second end member adapted to be coupled to second end portions of the first and second curved specimens. An approximately rigid member is disposed between the first and second end members. The approximately rigid member is adapted to be disposed between the first and second curved specimens and has a pair of curved outer surfaces adapted to be engaged against at least a portion of each of the first and second curved specimens between the first and second end portions thereof.

18 Claims, 3 Drawing Sheets

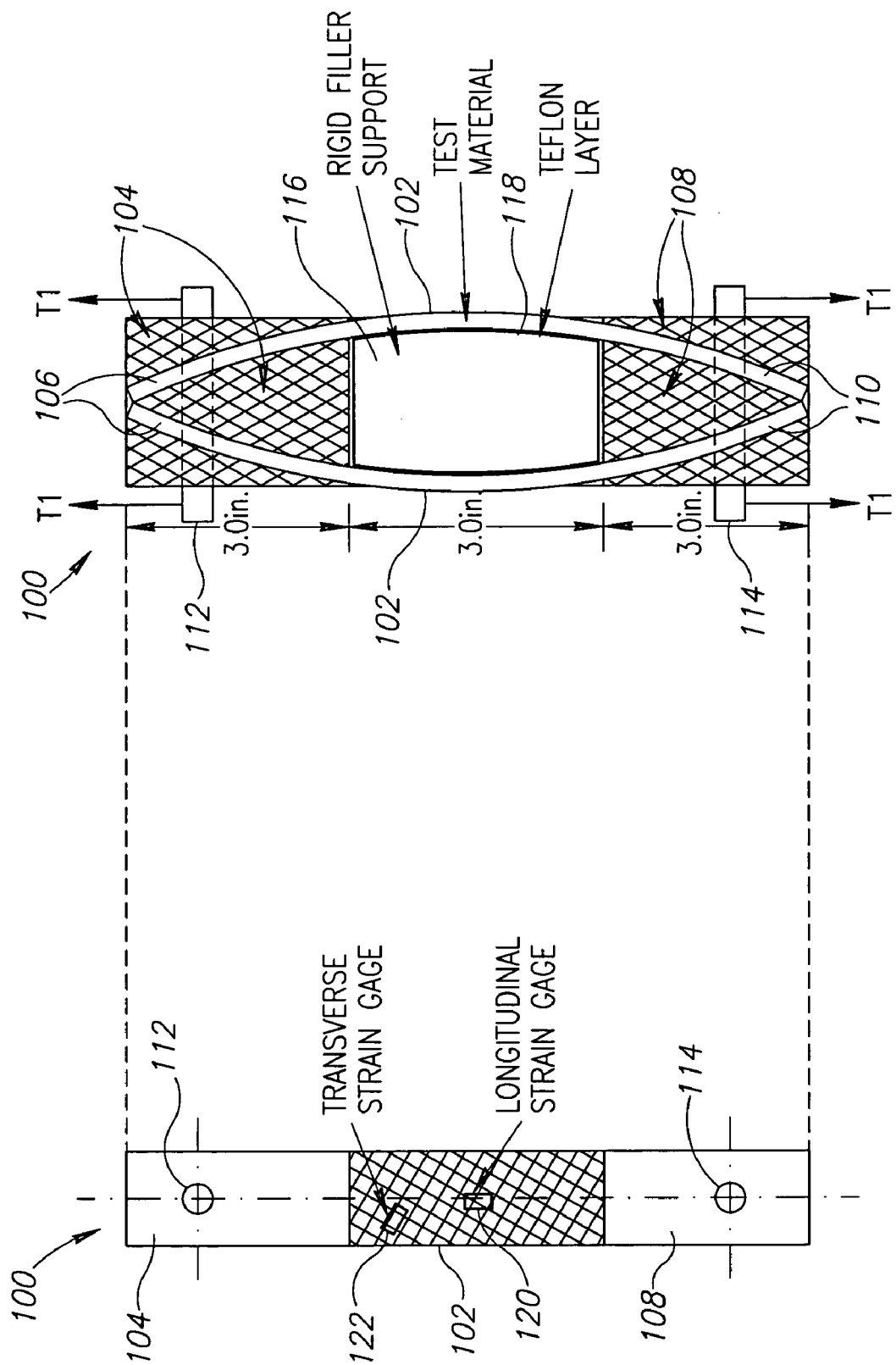

APPARATUS AND METHODS FOR TENSION TESTING OF CURVED SPECIMENS

FIELD OF THE INVENTION

The present disclosure relates to apparatus and methods for tension testing of curved specimens, and more specifically, to tension testing of curved composite material specimens without introducing bending.

BACKGROUND OF THE INVENTION

In various fields of engineering, the use of composite materials is widespread. In aerospace structures, for example, composite materials are used to fabricate a variety of curved, non-planar components, such as aerodynamic surfaces, domes, pressurized vessels, and the like. Although desirable results have been achieved using curved composite components, to continue to improve the reliability of such components, it is desirable to provide improved apparatus and methods of tension testing of segments from such curved composite components in such a way that the curved segment do not undergo any undesirable changes in shape due to the tension testing.

SUMMARY OF THE INVENTION

The present invention is directed to apparatus and methods for tension testing of curved specimens, and more specifically, to tension testing of curved composite material specimens without introducing bending. Apparatus and methods in accordance with the present invention may advantageously provide an improved capability for designing more reliable hardware, may reduce the number of iterations in analysis and design, and may reduce design verification testing, all of which may lead to lower cost, reduced cycle time, and reduced rejection rate.

In one embodiment, an apparatus for tension-testing first and second curved specimens includes a first end member adapted to be coupled to first end portions of the first and second curved specimens, and a second end member adapted to be coupled to second end portions of the first and second curved specimens. An approximately rigid member is disposed between the first and second end members. The approximately rigid member is adapted to be disposed between the first and second curved specimens and has a pair of curved outer surfaces adapted to be engaged against at least a portion of each of the first and second curved specimens between the first and second end portions thereof.

BRIEF DESCRIPTION OF THE DRAWINGS

The preferred and alternative embodiments of the present invention are described in detail below with reference to the following drawings.

FIG. 1 is a side elevational view of a test assembly for performing tension testing of curved composite specimens in accordance with an embodiment of the present invention;

FIG. 2 is a front elevational view of the test assembly of FIG. 1;

DETAILED DESCRIPTION OF THE INVENTION

Figure 3:
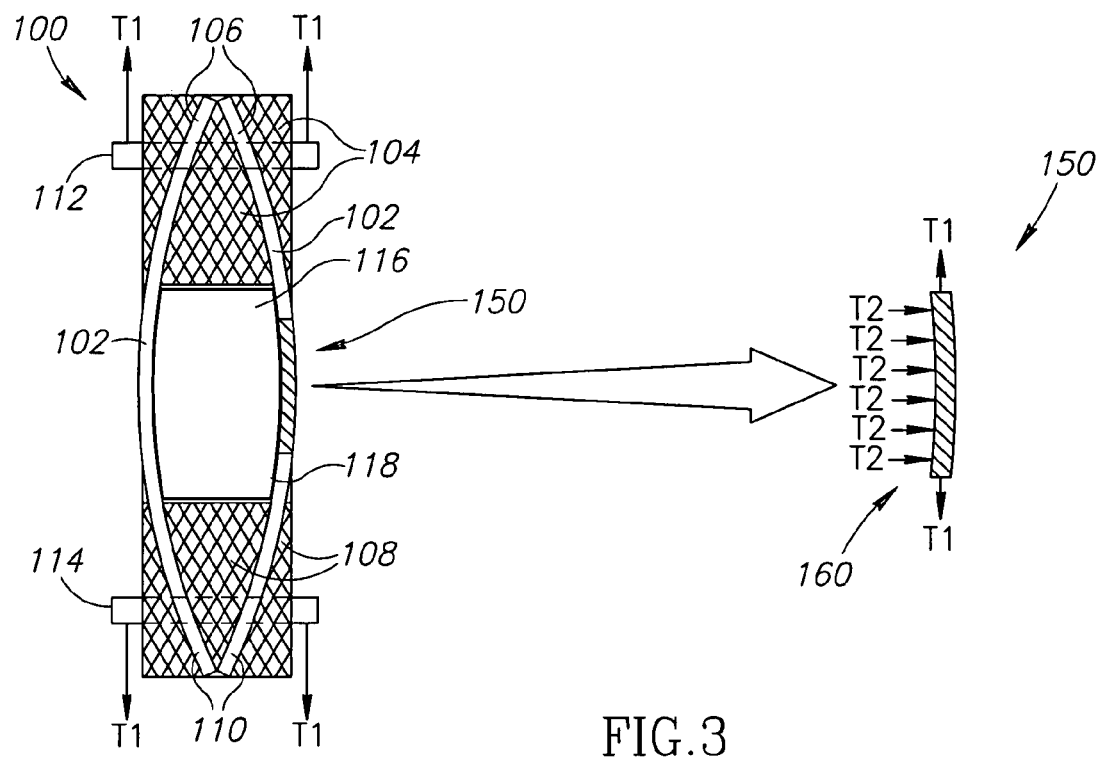
FIG. 3 is a front elevational view of the test assembly of FIG. 1 with an enlarged sectional view of a diagram of forces acting on a portion of a curved composite specimen during a test.

The present invention relates to apparatus and methods for tension testing of curved specimens, and more specifically, to tension testing of curved composite material specimens without introducing bending. Many specific details of certain embodiments of the invention are set forth in the following description and in FIGS. 1–6 to provide a thorough understanding of such embodiments. One skilled in the art, however, will understand that the present invention may have additional embodiments, or that the present invention may be practiced without several of the details described in the following description.

As described more fully below, in one embodiment, an apparatus for tension testing curved specimens includes two curved strips which are put together with convex surfaces facing each other and held together at both ends by adhesively bonded inner tabs. A cavity between the curved strips and the end tabs is occupied with a rigid member, the contact surfaces of which are provided with a low friction material. Apparatus and methods in accordance with the present invention provide valid tension testing of curved specimens, and an ability to test material from actual hardware. Furthermore, the use of a rigid "filler" in the cavity advantageously suppresses bending and simulates loading experienced by actual structures, such as a pressure vessel. The low friction material may help to insure that the rigid filler does not pick up any load that might distort the test results. Finally, embodiments of the present invention may be applicable to metals and composite components.

FIG. 1 is a side elevational view of a test assembly 100 for performing tension testing of curved composite specimens 102 in accordance with an embodiment of the present invention. FIG. 2 is a front elevational view of the test assembly 100 of FIG. 1. In this embodiment, the test assembly 100 includes upper tabs 104 surrounding upper ends 106 of the specimens 102, and lower tabs 108 surrounding lower ends 110 of the specimens 102. An upper pull member 112 is disposed through the upper tabs 104 and a lower pull member 114 is disposed through the lower tabs 108. A rigid member 116 is approximately centrally positioned between the upper and lower tabs 104, 108, and the test specimens 102. A layer of low-friction slip material 118 (e.g TEFLON®) is disposed between the rigid member 116 and the specimens 102. As shown in FIG. 1, longitudinal and transverse strain gages 120, 122 are applied on one or more lateral sides of the specimens 102.

FIG. 3 is a front elevational view of the test assembly 100 of FIG. 1 with an enlarged sectional view of a diagram of forces 160 acting on a portion 150 of the curved composite specimen 102 during a test. In operation, as a tension force T1 is applied to the upper and lower pull members 112, 114, a corresponding tension force T1 is formed in the portion 150 of the specimen 102, and corresponding reaction forces T2 are also formed that act outwardly against the portion 150 of the specimen 102.

Figure 4:
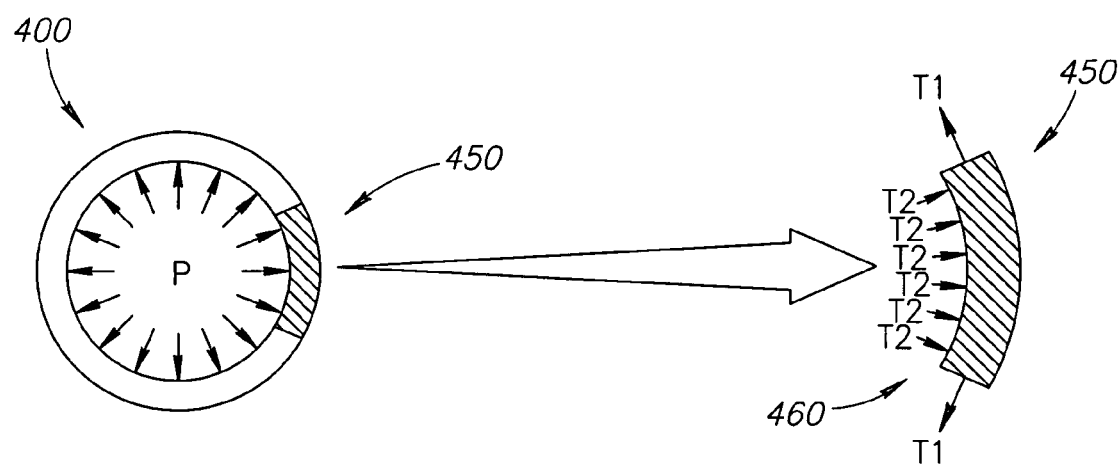
FIG. 4 is a top cross-sectional view of a pressure vessel and an enlarged sectional view of a diagram of the forces acting on a curved composite portion of the pressure vessel during operation.

For comparison, FIG. 4 shows a top cross-sectional view of a pressure vessel 400 and an enlarged sectional view of a diagram of the forces 460 acting on a curved composite portion 450 of the pressure vessel 400 during operation. In operation, a pressure P within the pressure vessel 400 exerts outward or transverse forces T2 against the portion 460, and generates circumferential (or hoop) tension forces T1 along the portion 460.

Thus, comparison of the force diagrams 360, 460 of FIGS. 3 and 4 shows that the test assembly 100 may advantageously provide tension forces T1 and transverse forces T2 on the portion 150 of the specimen 102 that accurately simulate the actual forces that may be encountered on the portion 150 in operation (e.g. as a pressure vessel 400). The longitudinal and transverse strain gages 120, 122 may thereby be used to collect test data on the transverse and longitudinal strains that develop within the specimens 102 as would occur during actual operating conditions.

Figure 5:
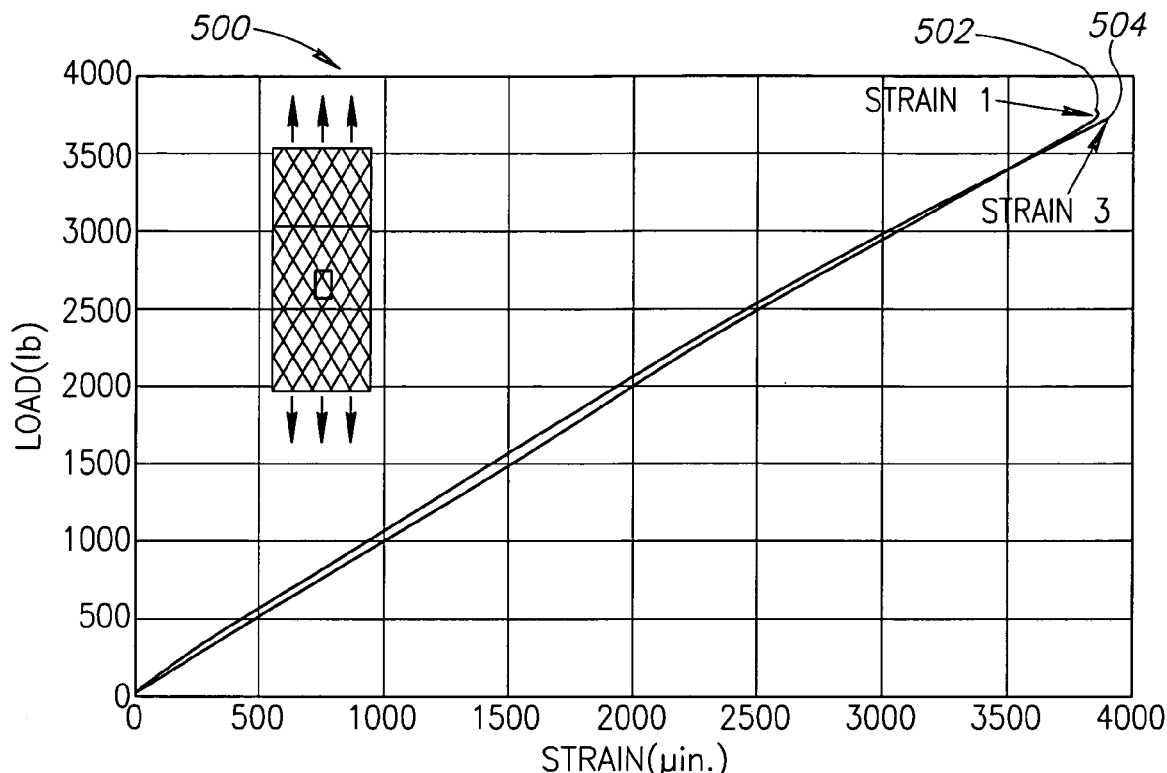
FIG. 5 is a graph of measured hoop strains measured in an axial or load direction within a curved composite specimen in accordance with an embodiment of the invention.
Figure 6:
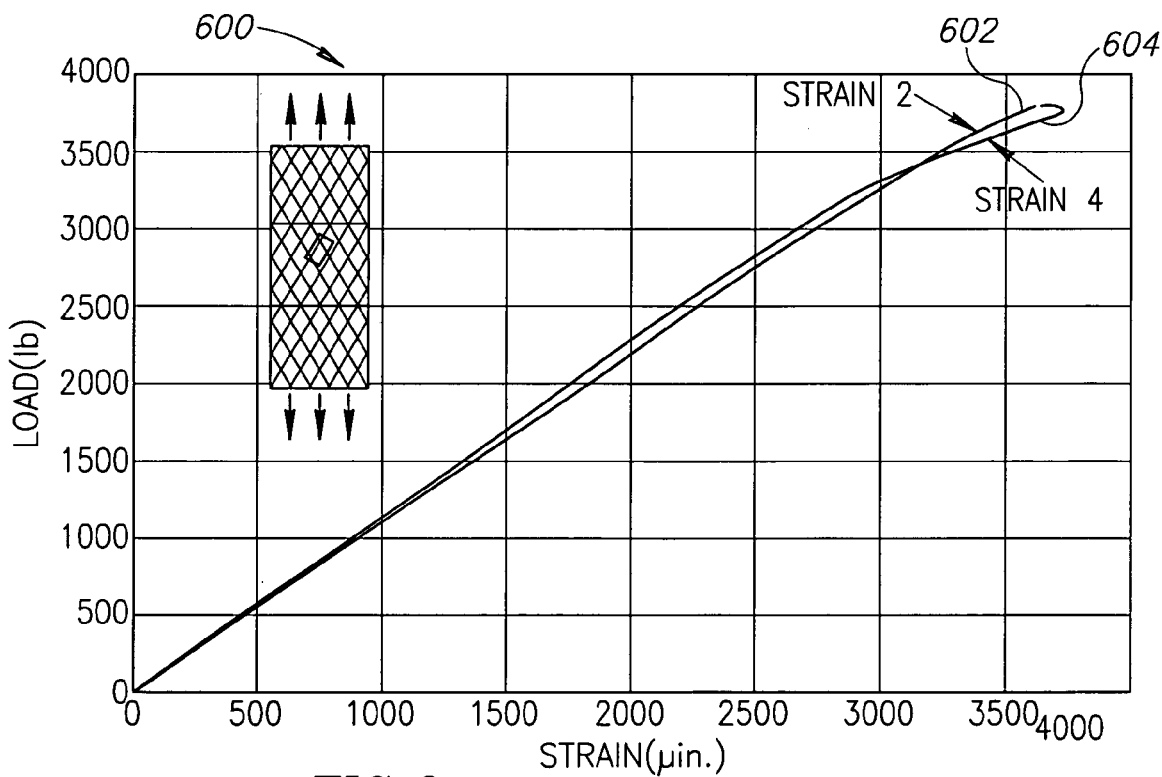
FIG. 6 is a graph of measured transverse to the fiber direction strains within a curved composite specimen in accordance with an embodiment of the invention.

FIG. 5 is a typical graph 500 of measured hoop strains 502, 504 measured in an axial or load direction within the curved composite specimens 102a, 102b, and FIG. 6 is a graph 600 of measured transverse to the fiber direction strains 602, 604 within the curved composite specimens 102a, 102b, in accordance with embodiments of the invention. As shown in FIG. 5, the measured hoop strains 502, 504 are very consistent between the two curved composite specimens 102a, 102b. Similarly, FIG. 6 shows that measured transverse strains 602, 604 show good agreement between the two curved composite specimens 102a, 102b.

Apparatus and methods in accordance with the present invention may advantageously improve manufacturing of curved composite components in several respects. For example, apparatus and methods in accordance with the present invention may provide an improved characterization of the axial and hoop strains that exist within a curved composite component under a given load in comparison with prior art methods and apparatus. Another advantage of the present invention is that the curved composite component may not undergo any undesirable changes in shape due to the tension testing. The inventive apparatus and methods may provide an improved capability for designing more reliable hardware, may reduce the number of iterations in analysis and design, and may reduce design verification testing, all of which may lead to lower cost, reduced cycle time, and reduced rejection rate.

While various preferred and alternate embodiments of the invention have been illustrated and described, as noted above, many changes can be made without departing from the spirit and scope of the invention. Accordingly, the scope of the invention is not limited by the disclosure of the preferred embodiment. Instead, the invention should be determined entirely by reference to the claims that follow.

What is claimed is:

1. An apparatus for tension-testing a plurality of curved specimens, comprising:
    a first curved specimen and a second curved specimen;
    a first end member coupled to first end portions of the first and second curved specimens;
    a second end member coupled to second end portions of the first and second curved specimens; and
    an approximately rigid member disposed between the first and second end members and disposed between the first and second curved specimens, the approximately rigid member having a pair of curved outer surfaces engaged against at least a portion of each of the first and second curved specimens between the first and second end portions thereof.

2. The apparatus of claim 1, wherein the curved outer surfaces of the approximately rigid member include a layer of low-friction material.

3. The apparatus of claim 1, wherein at least one of the first and second end members includes a pull member adapted to receive the applied test force.

4. The apparatus of claim 1, wherein the approximately rigid member is a symmetrical member.

5. The apparatus of claim 1, further comprising at least one strain gage adapted to be coupled to a surface of a corresponding at least one of the first and second curved specimens.

6. The apparatus of claim 1, wherein the at least one strain gage includes at least one of a longitudinal and a transverse strain gage.

7. An assembly for tension-testing a plurality of contoured specimens, comprising:
    a first contoured specimen and a second contoured specimen;
    a first support member coupled to first end portions of the contoured specimens;
    a second support member coupled to second end portions of the contoured specimens; and
    an approximately rigid member disposed between the first and second support members and disposed between the pair of contoured specimens, the approximately rigid member having a pair of contoured outer surfaces engaged along at least a portion of each of the contoured specimens between the first and second end portions thereof when a test force is applied to pull the first and second support members in substantially opposite directions.

8. The assembly of claim 7, wherein the contoured outer surfaces of the approximately rigid member include a layer of low-friction material.

9. The assembly of claim 7, wherein at least one of the first and second support members includes a pull member adapted to receive the applied test force.

10. The assembly of claim 7, wherein the approximately rigid member is a symmetrical member.

11. The assembly of claim 7, further comprising at least one strain gage adapted to be coupled to a surface of a corresponding at least one of the contoured specimens.

12. The assembly of claim 11, wherein the at least one strain gage includes at least one of a longitudinal and a transverse strain gage.

13. A method of simultaneously tension-testing a plurality of curved specimens, comprising:
    providing a pair of curved specimens;
    coupling a first end member to first and portions of the pair of curved specimens;
    coupling a second end member to second end portions of the pair of curved specimens;
    disposing an at least approximately rigid member between the first and second end members and between the pair of curved specimens;
    applying a test force that moves the first and second end members apart; and
    simultaneously with applying the test force, at least partially engaging the pair of curved specimens against a pair of curved outer surfaces of the at least approximately rigid member.

14. The method of claim 13, at least partially engaging the pair of curved specimens against a pair of curved outer surfaces includes at least partially engaging the pair of curved specimens against a layer of low-friction material on the outer surfaces.

15. The method of claim 13, wherein coupling a first end member includes coupling a first end member having a pull member adapted to receive the applied test force.

16. The method of claim 13, wherein disposing an at least approximately rigid member between the first and second end members includes disposing a symmetrical rigid member between the first and second end members.

17. The method of claim 13, further comprising measuring an axial strain in at least one of the first and second curved specimens.

18. The method of claim 13, further comprising measuring a transverse strain in at least one of the first and second curved specimens.

* * * * *